(12) United States Patent
Hartmann et al.

(10) Patent No.: US 6,984,737 B2
(45) Date of Patent: Jan. 10, 2006

(54) DI(HET)ARYLAMINOTHIOPHENE DERIVATIVES

(75) Inventors: Horst Hartmann, Merseburg (DE); Andreas Kanitz, Hoechstadt (DE); Wolfgang Rogler, Moehrendorf (DE); Jörg Schumann, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 10/181,744

(22) PCT Filed: Jan. 19, 2001

(86) PCT No.: PCT/DE01/00226

§ 371 (c)(1),
(2), (4) Date: Nov. 18, 2002

(87) PCT Pub. No.: WO01/53286

PCT Pub. Date: Jul. 26, 2001

(65) Prior Publication Data

US 2003/0137240 A1 Jul. 24, 2003

(30) Foreign Application Priority Data

Jan. 20, 2000 (DE) .......................... 100 02 424

(51) Int. Cl.
*C07D 333/36* (2006.01)
*C07D 409/00* (2006.01)

(52) U.S. Cl. .......................................... 549/68; 549/59
(58) Field of Classification Search ................. 549/68, 549/59
See application file for complete search history.

(56) References Cited

U.S. PATENT DOCUMENTS

| 4,539,507 | A | | 9/1985 | VanSlyke et al. |
| 5,247,190 | A | | 9/1993 | Friend et al. |
| 6,414,164 | B1 | * | 7/2002 | Afzali-Ardakani et al. ... 549/59 |
| 6,716,995 | B2 | * | 4/2004 | Huang et al. .................. 549/62 |

FOREIGN PATENT DOCUMENTS

| JP | 05158260 | 6/1993 |
| JP | 63183451 | 7/1998 |
| JP | 10219242 | 8/1998 |

OTHER PUBLICATIONS

Yu et al., "New efficient blue light emitting polymer for light emitting diodes" *Chem. Comm.* 1837–1838, 1999.
Rompp Chemie–Lexikon, $9^{th}$ edition, p. 1750.
Rompp Chemie–Lexikon, $9^{th}$ edition, p. 2464.
Rompp Chemie–Lexikon, $9^{th}$ edition, p. 4796.

* cited by examiner

*Primary Examiner*—Deborah C. Lambkin
(74) *Attorney, Agent, or Firm*—Fish & Richardson P.C.

(57) ABSTRACT

The invention relates to novel 2-(N,N-di(het)arylamino)-thiophene derivatives of formula (I), wherein $R^1$, $R^2$, $R^3$, $R^4$ and $R^5$ are, independently each of other, each a monofunctional (het)aryl system and wherein $R^1$ can also be a bifunctional (het)arylene system, $R^3$ can also be a group $R^8$, except when $R^1$ is a bifunctional (het)arylene system, $R^8$ representing chemical bond or a bifunctional (het)arylene system, $R^4$ can also mean $R^{10}$, $R^{10}$ representing a chemical bond or a bifunctional (het)arylene system, or $R^4$ can be one of the following groups (II) and (III), $R^9$ representing a chemical bond or a bifunctional (het)arylene system and $R^5$ can also be H or (IV).

10 Claims, No Drawings

DI(HET)ARYLAMINOTHIOPHENE DERIVATIVES

The invention relates to novel di(het)arylaminothiophene derivatives, i.e. diarylaminothiophene or dihetarylaminothiophene derivatives ("hetaryl"="heteroaryl"), and their preparation and use.

For organic light-emitting diodes (organic LEDs=OLEDs) and organic photovoltaic components, organic materials which are capable of electroluminescence are required. These may be either compounds having a small molecular size (cf. for example U.S. Pat. No. 4,539,507) which are vaporizable or polymeric materials (cf. for example U.S. Pat. No. 5,247,190) which can be processed by spin-coating.

The synthesis of compounds of said type requires aromatic coupling reactions. Such reactions, in which halogen-containing compounds are used, take place in some cases under metal catalysis, for example according to a Heck reaction or according to a Suzuki reaction (in this context, cf.: "Chem. Commun.", 1999, pages 1837 to 1838). Here, however, it is scarcely possible completely to remove the metal, such as palladium (in this context, cf.: "Römpp Chemie-Lexikon", 9th edition, page 1750). However, metals—and traces of halogen-containing intermediates not completely reacted—act as so-called quenchers, i.e. they quench the electroluminescence in their environment, and they therefore greatly reduce the efficiency of the materials produced.

In the case of aromatic coupling corresponding to an Ullmann reaction (in this context, cf.: "Römpp Chemie-Lexikon", 9th edition, page 4796), the formation of byproducts and of crack products, which arise owing to high process temperatures, is a major problem. In fact, the purification of the reaction product to an acceptable extent is scarcely possible or not possible at all.

The invention therefore relates to novel 3,4-substituted 2-(N,N-di(het)arylamino)thiophene derivatives of the general structure

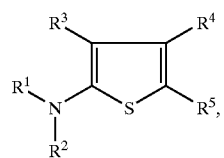

in which the following is applicable:

$R^1$, $R^2$, $R^3$, $R^4$ and $R^5$—independently of one another—are each a monofunctional (het)aryl system, i.e. a conjugated carbocyclic or heterocyclic ring system which may also comprise identical or different ring types which are linked or fused on linearly or at angles, it being possible for the peripheral hydrogen atoms to be substituted by alkyl, alkoxy, phenoxy, dialkylamino or diphenylamino groups (alkyl=$C_1$ to $C_6$);

$R^1$ may furthermore be a corresponding bifunctional (het)aryl system, i.e. a conjugated carbocyclic or heterocyclic ring system which may also comprise identical or different ring types linked or fused on linearly or at angles, it being possible for the peripheral hydrogen atoms to be substituted by alkyl, alkoxy, phenoxy, dialkylamino or diphenylamino groups (alkyl=$C_1$ to $C_6$);

$R^3$ may furthermore be a group $R^8$, except if $R^1$ is a bifunctional (het)arylene system, $R^8$ representing a chemical bond or a bifunctional (het)arylene system;

$R^4$ may furthermore denote $R^{10}$, $R^{10}$ representing a chemical bond or a bifunctional (het)arylene system, or $R^4$ may be one of the following groups:

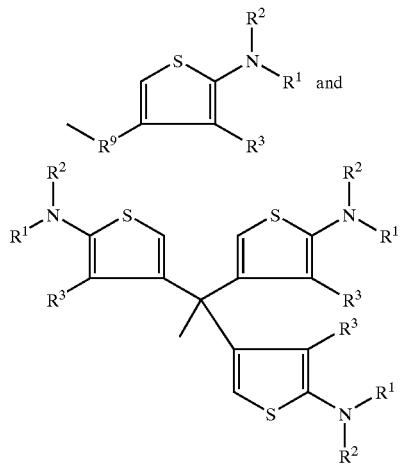

$R^9$ representing a chemical bond or a bifunctional (het)arylene system;

$R^5$ may also be H or

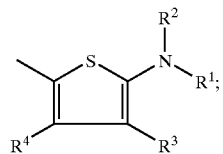

the following may furthermore be the case:

$R^4$ and $R^5$ together form one of the following groups:

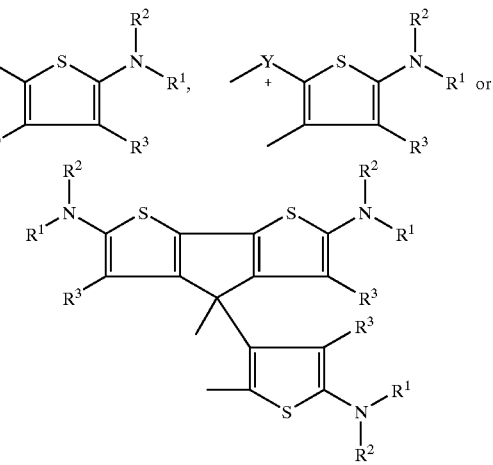

$R^4$ and $R^1$ together form the following group:

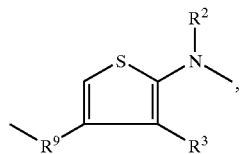

$R^4$ and $R^3$ together form the following group:

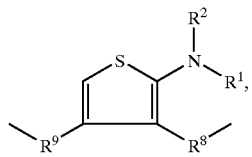

$R^5$ and $R^1$ together form the following group:

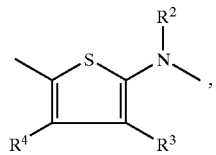

$R^5$ and $R^3$ together form the following group:

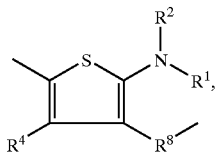

$R^5$, $R^4$ and $R^1$ together form one of the following groups:

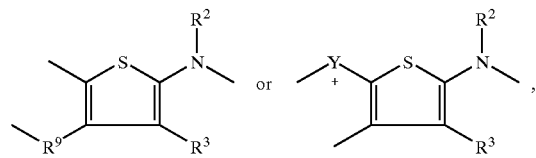

$R^5$, $R^4$ and $R^3$ together form the following group:

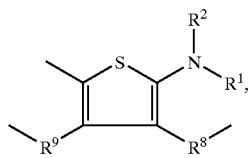

Y in each case denoting CH or N.

The preparation of the novel di(het)arylaminothiophene derivatives is carried out by means of a hetaryl cyclization reaction under mild conditions and without metal catalysts. These compounds can therefore be prepared in high purity, i.e. the efficiency of these materials, in particular the electroluminescence, is not adversely affected by impurities which are present in compounds prepared by known processes, for example owing to the catalyst used. A further advantage of these materials consists in improved redox properties adaptable to the respective purpose, owing to the wide range of possible structures which arise from the synthesis principle described in more detail below. This synthesis principle furthermore makes it possible to obtain the novel materials without problems, also in the form of oligomer and polymer structures, i.e. to prepare oligo- and polyaminothiophene derivatives.

The synthesis of the novel compounds requires in some cases precursors which have not been known to date. However, these precursors are obtainable—from commercially available starting materials—in virtually quantitative yield.

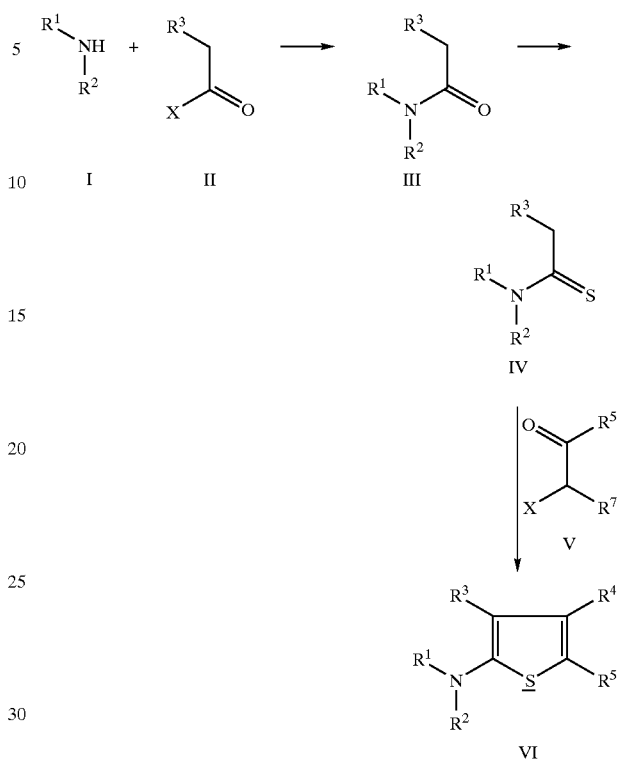

The following is applicable here:
$R^1$, $R^2$, $R^3$, $R^4$ and $R^5$ have the abovementioned meaning;
$R^6$ and $R^7$—independently of one another—are each a monofunctional (het)aryl system, i.e. a conjugated carbocyclic or heterocyclic ring system, which may also comprise identical or different ring types linked or fused on linearly or at angles, it being possible for the peripheral hydrogen atoms to be substituted by alkyl, alkoxy, phenoxy, dialkylamino or diphenylamino groups (alkyl=$C_1$ to $C_6$);
$R^6$ may furthermore be the group $R^9$, the compound V carrying, at the free bond, a group —CO—CH$_2$X where X=halogen, preferably Cl, Br or I,
or $R^6$ may be a group —C(CO—CH$_2$X)$_3$.

The first stage of the synthesis of the thiophene derivatives comprises the reaction of a secondary amine I with an acyl halide II to give a carboxamide (acid amide) III. The reaction is carried out in a suitable solvent, preferably dioxane, at elevated temperature, preferably in the region of the boiling point of the solvent, under inert gas. The reaction is stopped when the hydrohalide (hydrogen halide) formed as the byproduct is removed by the inert gas stream or when no more amine is detectable, for example by checking by thin-layer chromatography.

The acid amide III is then converted into a thiocarboxamide (thioamide) IV in a second stage. This is advantageously effected by means of the so-called Lawesson reagent, a reagent which acts in the homogeneous phase for introducing sulfur into carbonyl compounds (in this context, cf.: "Römpp Chemie-Lexikon", 9th edition, page 2464), in a suitable solvent, preferably diglycol diethyl ether, at elevated temperature, preferably at about 100° C.; duration: several hours, in general about 6 h. However, the sulfur can also be introduced in the heterogeneous phase, for example by means of phosphorus pentasulfite.

In a third stage, the thioamide IV—depending on the substitution pattern (cf. IVa to IVc below)—is converted into a semiconducting 3,4-substituted 2-(N,N-di(het)arylamino)thiophene derivative VI by reaction with an α-haloacyl compound V in a suitable solvent, preferably methylene chloride, dichloroethane, acetic anhydride, dimethylformamide or tetrahydrofuran, depending on the substitution pattern of the acyl compound (cf. Va to Vd below). This is effected by a primary S-alkylation and a subsequent cyclization (ring closure reaction) and aromatization. The cyclization can be accelerated by adding a deprotonating agent, preferably triethylamine.

Thiophene derivatives VI which are unsubstituted in the 5-position, i.e. $R^5$=H, can be converted by oxidative coupling into dimeric or polymeric derivatives VI (cf. VIg, h, i, n, r, s, t, v and z below), which are likewise semiconductor materials. The oxidative coupling is effected in a suitable solvent, preferably dry tetrahydrofuran, by oxidizing agents known per se, preferably by oxidation of the respective thiophene derivative, converted into the lithium compound by means of butyllithium, with copper(II) chloride or by electrooxidation on a conductive substrate, for example on a glass plate coated with ITO (ITO=indium tin oxide).

By means of halogenated 1,2-diketones (cf. Vd/d below)—as the α-haloacyl compound—thiophene derivatives VI which are prepared from the thiocarboxamides IV and are unsubstituted in the 5,5'-position and linked in the 4,4'-position (cf. VIw and VIx below) can be converted, with orthoformic esters or with nitrous acid, which is generated, for example, from sodium nitrite or isoamyl nitrite, into corresponding cationic hole transport materials (cf. VI/1 and VI/2 below) which are analogous to the known polythiophenes and polyanilines in their property as organic conductors.

The structural formulae of a relatively large number of the novel thiophene derivatives—together with the direct starting materials—are shown below in table form.

| Organically semiconducting products from the combinations of thiocarboxamides IV and □-haloacyl compounds V and their oxidation products and conductive cationic structures | 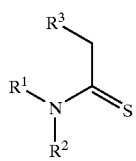 |
| --- | --- |
| | IVa |
| Oxidation | 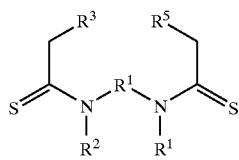 |
| | IVb |
| 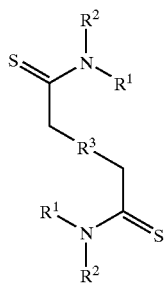 | 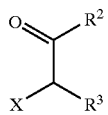 |
| IVc | Va |
| 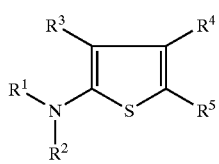 | 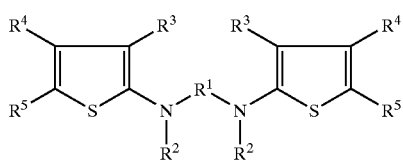 |
| VIa | VIb |

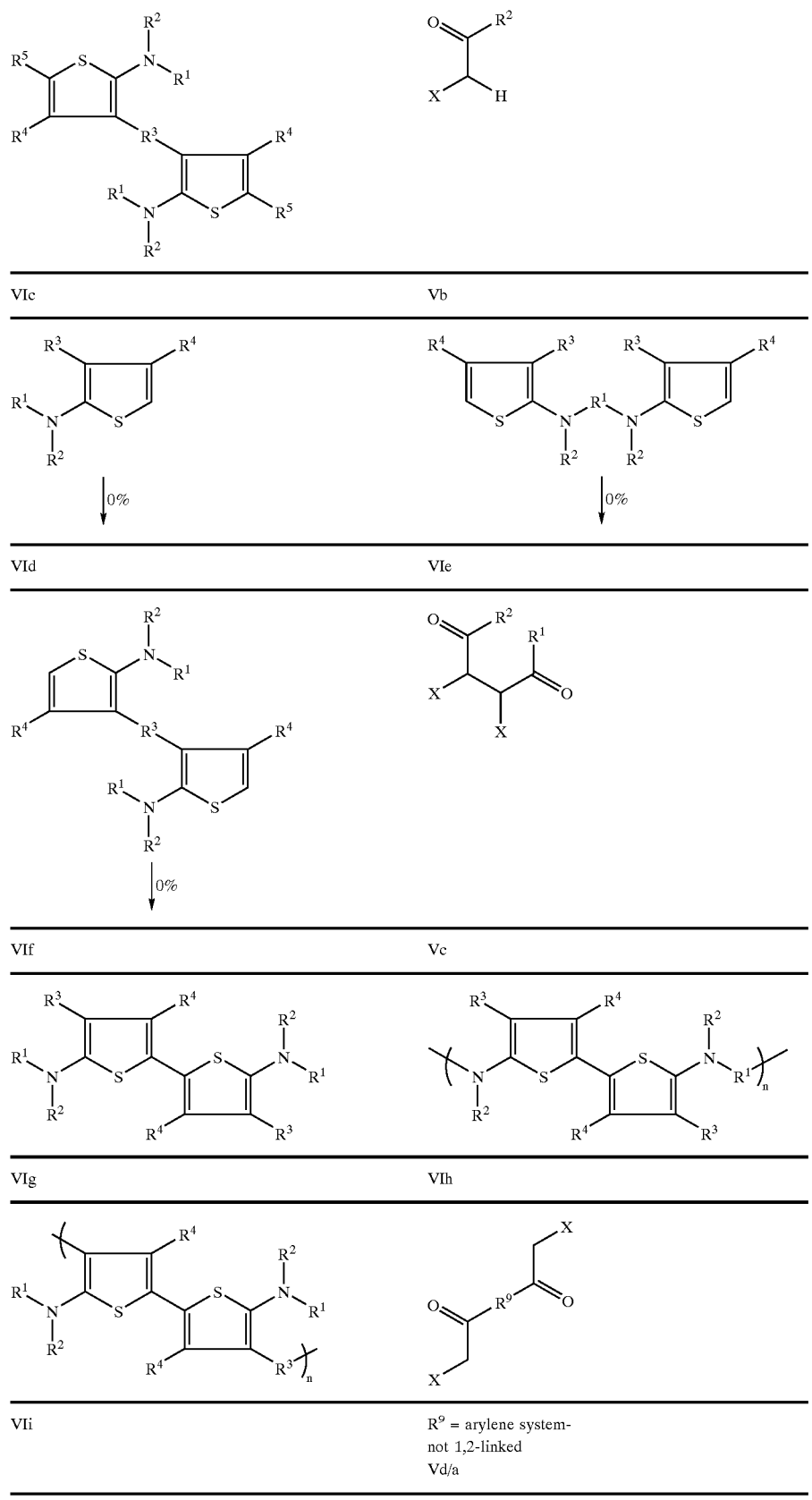

-continued
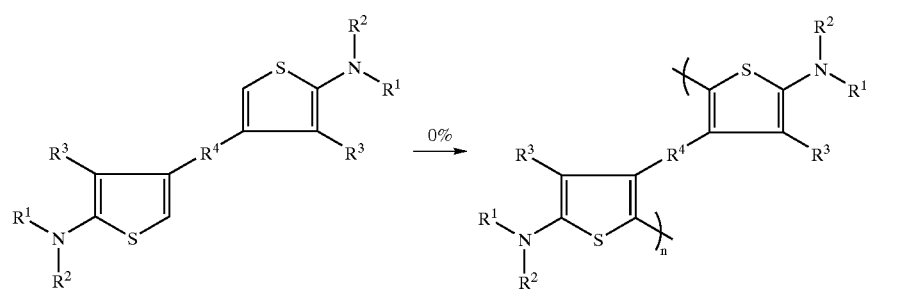
| VIk | VIn |
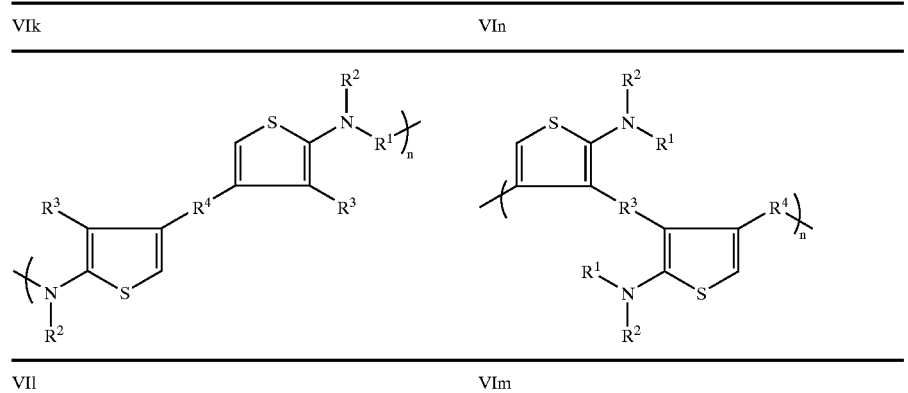
| VIl | VIm |
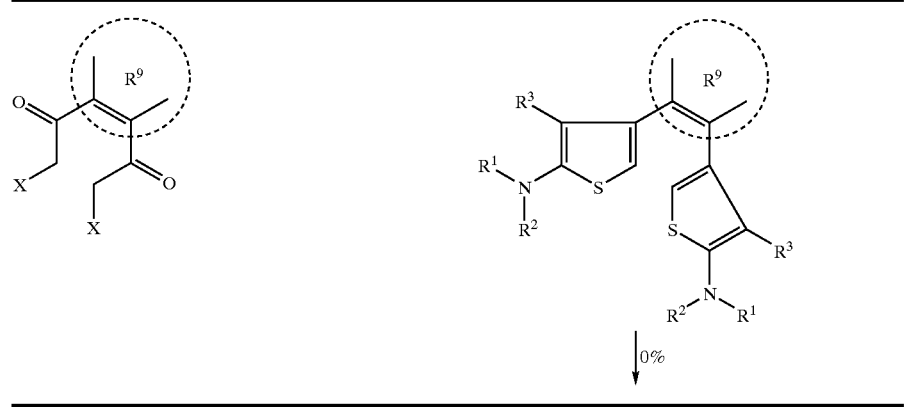
| $R^9$ = arylene system- not 1,2-linked Vd/b | VIo |
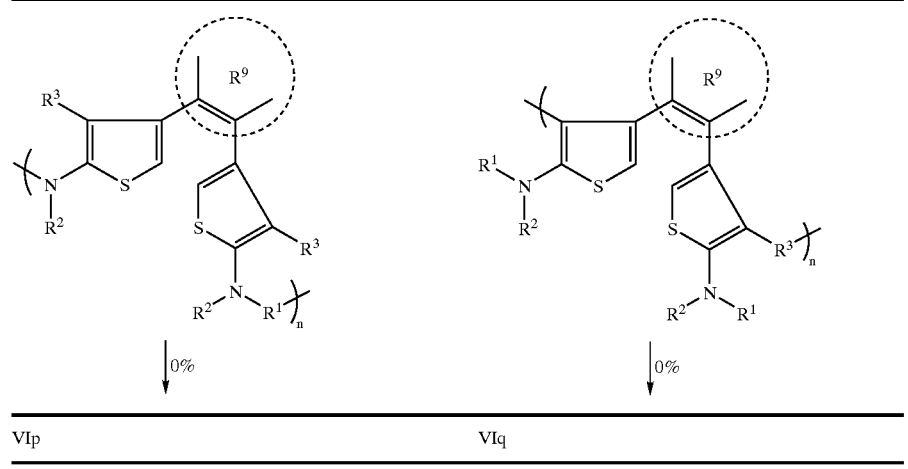
| VIp | VIq |

-continued
Oxidation
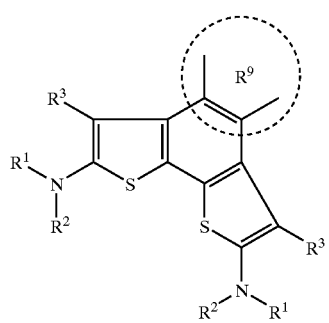
VIr
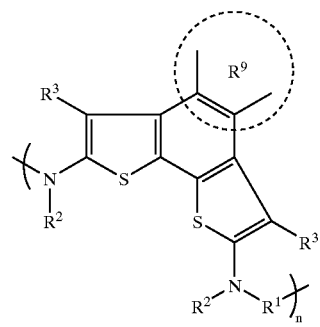
VIs
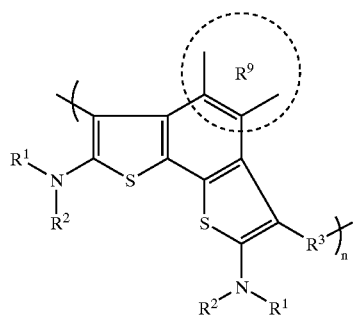
VIt
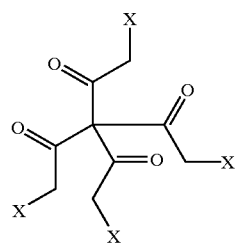
$R^6 = -C(CO-CH_2X)_3$
Vd/c
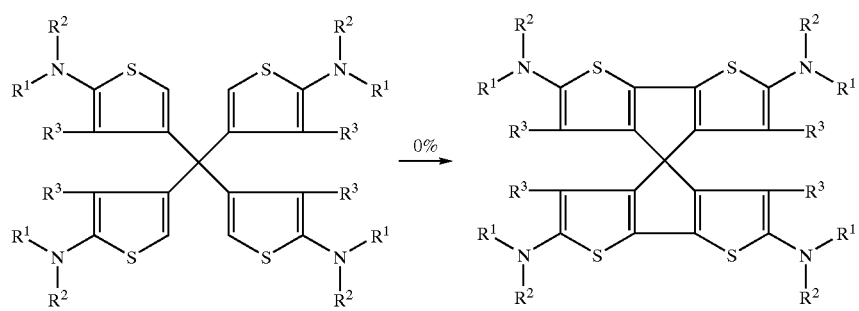
VIu    VIv

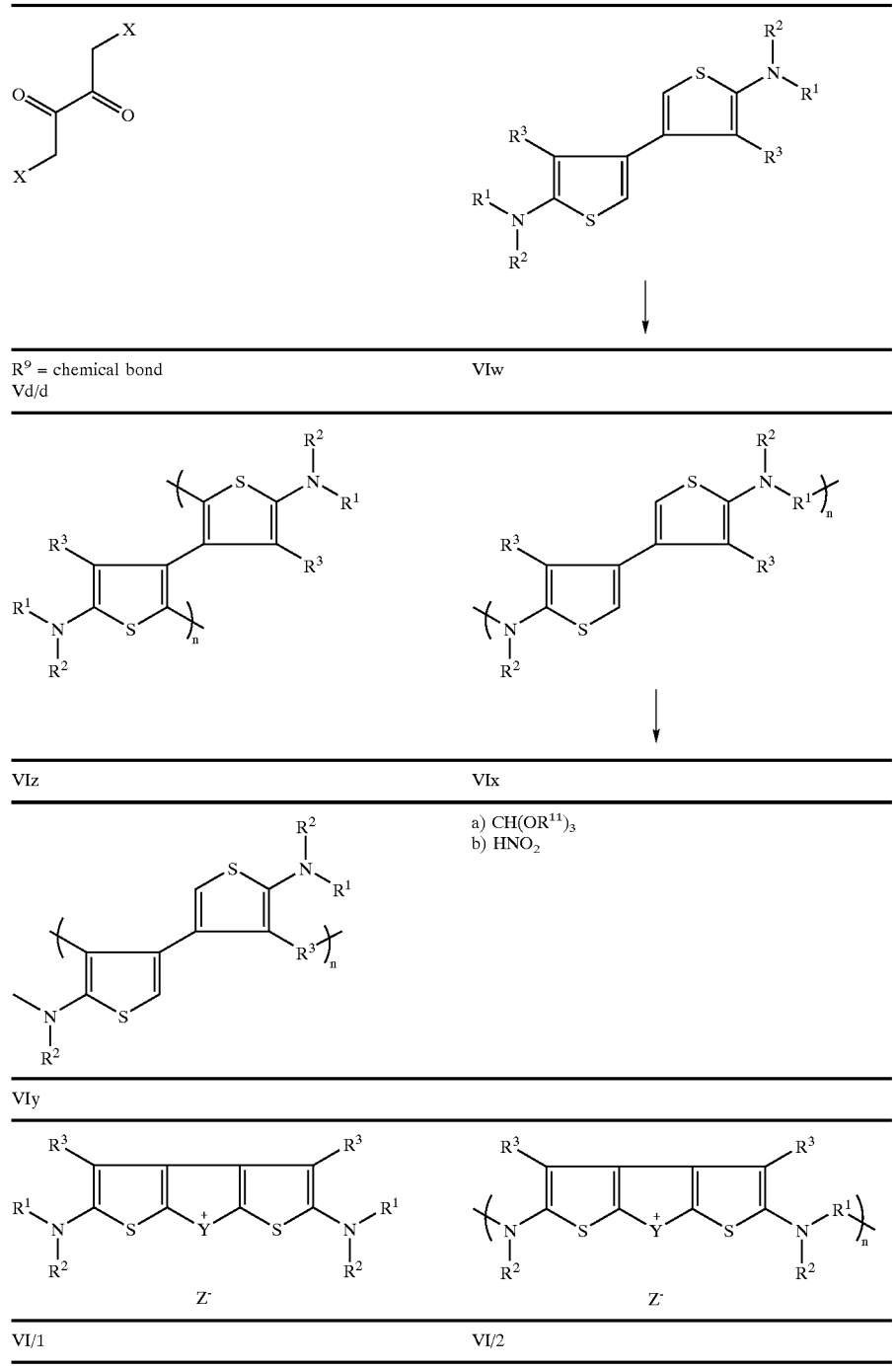

$R^{11}$ is an alkyl radical having 1 to 5 C atoms, $Z^-$ is any desired anion, preferably a polystyrene-sulfonate or another organic sulfonate, n denotes in each case an integer from 2 to 100.

The thiophene derivatives according to the invention of the type VI are all suitable materials for the synthesis of organic light-emitting diodes (OLEDS) and organic photovoltaic components or cells. They can be used both in hole transport layers or layer cascades and in emitter and electron transport layers. The respective layer position in OLEDs is determined in particular by the (het)aryl or (het)arylene members; the more of these members have a π-electron deficiency, i.e. so-called π-deficient aromatics, the more suitable are the thiophene derivatives as emitter and electron transport materials.

The following types of compounds are particularly preferred:

VIb, VIc, VIe, VIf, VIg, VIh, VIi and VIk;
VIr;
VIv;
VI/1 and VI/2.

Both OLED materials which are suitable as vaporizable compounds for so-called "small molecule devices" and polymer materials processible by spin-coating and intended for so-called "polymer devices" can be realized via the synthesis route described; the nonpolymeric materials can likewise be processed by spin-coating. Owing to the common parent structure of all materials, corresponding copolymers having tailored electronic properties can also advantageously be prepared. It is furthermore possible to realize the electronic properties required for the respective intended use by mixtures of corresponding materials which—owing to the structural similarity—are very compatible with one another. Materials tailored in this manner therefore permit a single-layer structure of OLEDs, which is very advantageous. Glass transition temperatures of the charge transport and emitter materials prepared in the manner described, which are very high compared with known carbocyclic charge transport materials and are in general about 50 to 100° C. higher than those of the analogous carbocyclic compounds, are also remarkable.

The invention is to be explained in more detail with reference to exemplary embodiments.

EXAMPLE 1
Synthesis of Carboxamides III

In a 2 l three-necked flask having a reflux condenser, magnetic stirrer, dropping funnel and inert gas flow-through, in each case 1 mol of a secondary amine I is dissolved in 600 ml of dioxane. The acyl halide II required in each case is then added dropwise in an equivalent amount. The reaction mixture is then refluxed until the total amount of the hydrohalide formed in the reaction has been removed by the inert gas stream. The end of the reaction can additionally be detected by checking by means of thin-layer chromatography. The reaction solution is then cooled and is stirred into at least twice the amount of water. In most cases an oil separates out, which solidifies after a few hours. The aqueous phase is separated off and the crude product is recrystallized from ethanol. The yield is at least 90% in each case.

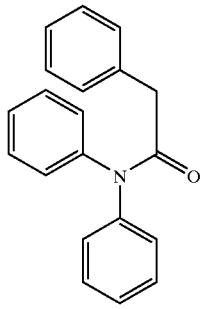

For example, N,N-diphenyl-2-phenylacetamide (m.p.: 71–72° C.) is prepared in this manner from diphenylamine and 2-phenylacetyl chloride.

EXAMPLE 2
Synthesis of Thiocarboxamides IV 0.5 mol of the respective carboxamide III and the equivalent amount of Lawesson reagent (prepared from anisole and phosphorus pentasulfide) are suspended in 750 ml of diglycol diethyl ether in a reflux apparatus with inert gas flow-through, and stirring is then carried out for 6 h at 100° C. A clear solution forms, from which the reaction product crystallizes out at room temperature in some cases. In order to isolate the product completely, the reaction mixture is stirred into twice the amount of water, and the oily phase which often forms is then allowed to crystallize, Thereafter, the product is separated from the aqueous phase and recrystallized from methanol. The yield is at least 90% in each case.

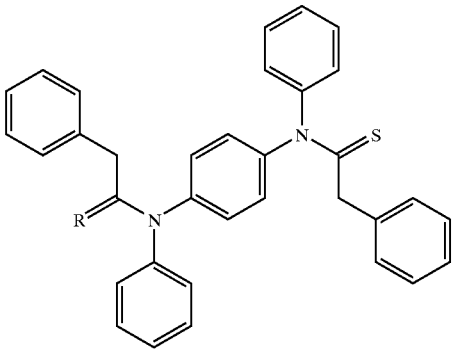

For example, the thiocarboxamide IVb ($R^1$=1,4-phenylene and $R^2$=$R^3$=phenyl) (m.p.: 225–227° C., $M^+$=528) is prepared in this manner from the carboxamide III ($R^1$=1,4-phenylene and $R^2$=$R^3$=phenyl).

EXAMPLE 3
Synthesis of Thiophene Derivatives VI

In a flask which is provided with a stirrer and reflux condenser, 0.1 mol of the respective thiocarboxamide IV are dissolved, together with the equivalent amount of an α-haloacyl compound V, in 200 ml of DMF, after which heating to 100° C. is carried out for 1 h. 0.1 mol of triethylamine are then added and heating is carried out for a further 30 min. After cooling, the resulting thiophene derivative is isolated by precipitation with ethanol, in some cases also with water, and filtration with suction. The crude product is purified by dissolving in THF and precipitating with ethanol. The yield is between 60 and 80% in each case.

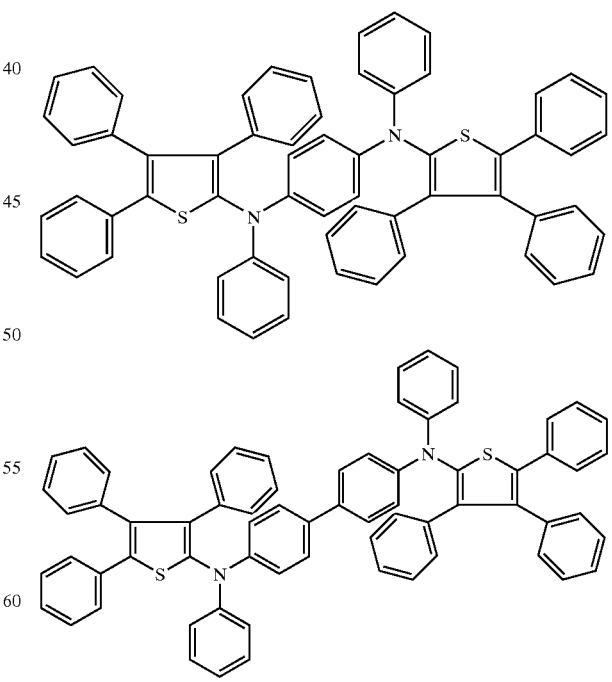

For example, the thiophene derivative VIb ($R^1$=1,4-phenylene and $R^2$=$R^3$=$R^4$=$R^5$=phenyl) (m.p.: 318° C., $T_g$=275° C., $M^+$=880) is prepared in this manner from the thiocarboxamide IVb ($R^1$=1,4 phenylene and $R^2$=$R^3$= phenyl) and desyl chloride (α-chloro-α-phenylacetophenone), and the thiophene derivative VIb ($R^1$=1,4-biphenylene and $R^2$=$R^3$=$R^4$=$R^5$=phenyl) (m.p.: 285° C. ° C., $T_g$=270° C., $M^+$=956) is prepared in this manner from the thiocarboxamide IVb ($R^1$=1,4 biphenylene and $R^2$=$R^3$= phenyl) and desyl chloride (α-chloro-α-phenylacetophenone).

The following procedure is used for the preparation of polymeric thiophene derivatives VI, for example VIh ($R^1$= 1,4-phenylene and $R^2$=$R^3$=$R^4$=phenyl):

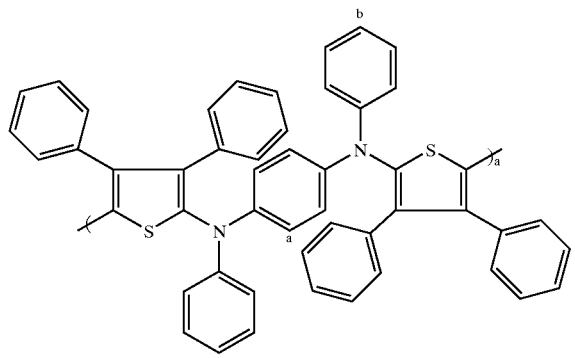

$^1$H-NMR: a=6.90 ppm (d), b=7.10 ppm (t), (DMF-$D_6$)

In a flask which is provided with stirrer and reflux condenser, 0.1 mol of thiocarboxamide IVb ($R^1$=1,4-phenylene, $R^2$=$R^3$=phenyl) are dissolved, together with 0.1 mol of dimeric phenacyl bromide Vc ($R^2$=phenyl), in 200 ml of DMF, after which heating to 100° C. is carried out for 1 h. For blocking terminal groups, a monofunctional vinylogous thioamide and a monofunctional acyl halide are then added in succession, in the present case first 0.01 mol of N,N-diphenyl-2-phenylthioacetamide and, after 60 min, 0.01 mol of phenacyl bromide. After a further 60 min, 0.1 mol of triethylamine are added and, after a further 15 min, the mixture is allowed to cool, the polymeric thiophene derivative formed being precipitated. The further working-up is carried out in the manner described above; yield: about 80%.

EXAMPLE 4
Synthesis of Dimeric or Polymeric Thiophene Derivatives VI (by Oxidative Coupling)

In a flask which is provided with a reflux condenser, stirrer, solids metering means and inert gas flow-through, 0.01 mol of a thiophene derivative VI unsubstituted in the 5-position are dissolved in 100 ml of dried THF. Cooling to −60° C. is effected, and then 0.015 mol of butyllithium are added. Thereafter, the cooling is removed and the reaction mixture is allowed to thaw at up to −10° C. 0.011 mol of copper(II) chloride are then added by the solids metering means, and further heating is then carried out to 40° C. The reaction is stopped after 30 min by precipitating the product with water (in the case of polymers, with methanol with the addition of 10% of water) and is then filtered off with suction. The product is purified by repeated dissolution in THF and precipitation with methanol. Nonpolymeric compounds can also be purified by sublimation.

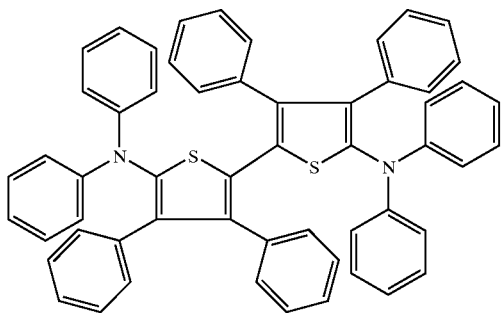

For example, the dimeric thiophene derivative VIg ($R^1$= $R^2$=$R^3$=$R^4$=phenyl) (m.p.: 255–285° C., $M^+$=804) is prepared in this manner from 2-diphenylamino-3,4-diphenylthiophene VId.

EXAMPLE 5
Synthesis of Thiophene Derivatives VI in the Form of Cationically Conductive Materials (Y=CH)

In a beaker, 0.01 mol of a dimeric thiophene derivative VI linked in the 4,4'-position and unsubstituted in the 5,5'-position are dissolved in 100 ml of DMF, and 0.015 mol of triethyl orthoformate are added. After the addition of 0.01 mol of perchloric acid and heating to about 100° C., a colored salt absorbing in the long-wave range forms, which salt, after the addition of ethanol and possibly a little ether, is precipitated and then filtered off with suction. By reacting the perchlorate dye with a solution of sodium polysytrenesulfonate, an aqueous solution of the respective cationically conductive material is obtained as polystyrene-sulfonate; this solution can be processed by spin-coating.

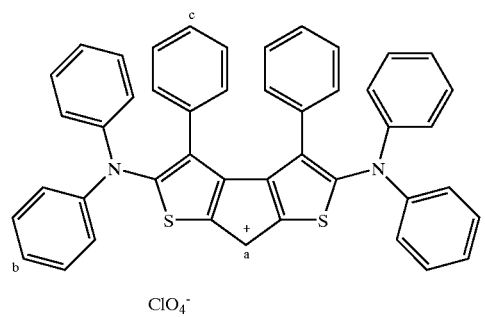

$^1$H-NMR: a=7.20 ppm (s), b=7.60 ppm (t), c=7.40 ppm (t) (DMSO-$D_6$) $\lambda_{max}$=687 nm For example, the thiophene derivative VI/1 ($R^1$=$R^2$=$R^3$= phenyl and Y=CH) ($M^+$=663) is prepared in this manner from the thiophene derivative VIw ($R^1$=$R^2$=$R^3$=phenyl) and triethyl orthoformate in the presence of perchloric acid.

EXAMPLE 6
Synthesis of Thiophene Derivatives VI in the Form of Cationically Conductive Materials (Y=N)

In a beaker, 0.01 mol of a dimeric thiophene derivative VI linked in the 4,4'-position and unsubstituted in the 5,5'-position are dissolved in 100 ml of THF, and 0.015 mol of isoamyl nitrate is added. After the addition of 0.01 mol of perchloric acid with cooling and subsequent heating to about 50° C., a colored salt absorbing in the long-wave range forms, which salt, after the addition of ethanol and possibly a little ether, is precipitated and then filtered off with suction. By reacting the perchlorate dye with a solution of sodium polystyrenesulfonate, an aqueous solution of the respective cationically conductive material is obtained as polystyrenesulfonate; this solution can be processed by spin-coating.

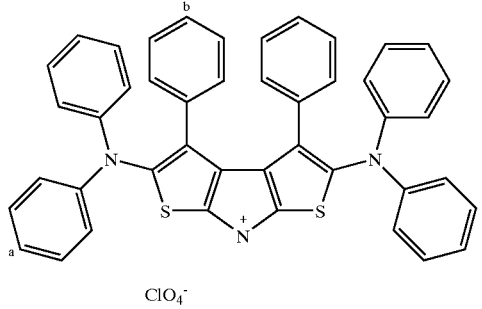

ClO$_4^-$ $^1$H-NMR: a=7.65 ppm (t), b=7.55 ppm (t), (DMSO-D$_6$) $\lambda_{max}$=750 nm For example, the thiophene derivative VI/1 (R$^1$=R$^2$=R$^3$=phenyl and Y=N) (M$^+$=664) is prepared in this manner from the thiophene derivative VIw (R$^1$=R$^2$=R$^3$=phenyl) and isoamyl nitrite in the presence of perchloric acid.

What is claimed is:

1. A 2-(N,N-di(het)arylamino) thiophene derivative of the structure

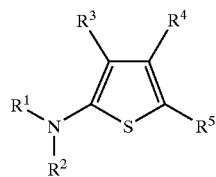

wherein:
R$^1$, R$^2$, R$^3$, R$^4$ and R$^5$—independently of one another—are each a monofunctional (het)aryl system, in the form of a conjugated carbocyclic or heterocyclic ring system which may also comprise identical or different ring types which are linked or fused on linearly or at angles, it being possible for the peripheral hydrogen atoms to be substituted by alkyl, alkoxy, phenoxy, dialkylamino or diphenylamino groups (alkyl=C$_1$ to C$_6$);

R$^1$ may furthermore be a corresponding bifunctional (het)aryl system,

R$^3$ may furthermore be a group R$^8$, except if R$^1$ is a bifunctional (het)arylene system, R$^8$ representing a chemical bond or a bifunctional (het)arylene system;

R$^4$ may furthermore denote R$^{10}$, R$^{10}$ representing a chemical bond or a bifunctional (het)arylene system, or R$^4$ may be one of the following groups:

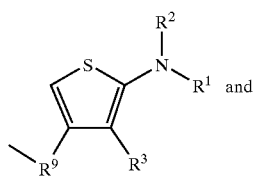 and

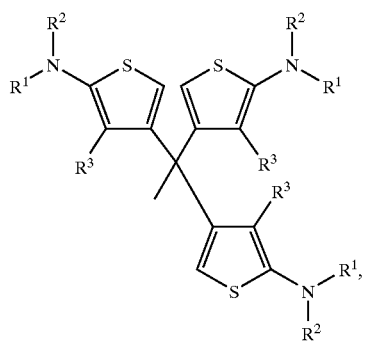

R$^9$ representing a chemical bond or a bifunctional (het)arylene system;

R$^5$ may also be H or

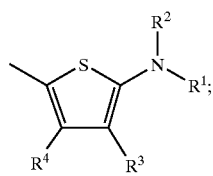;

the following may furthermore be the case:

R$^4$ and R$^5$ together form one of the following groups:

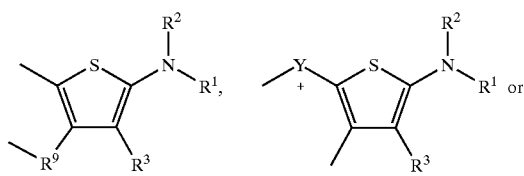

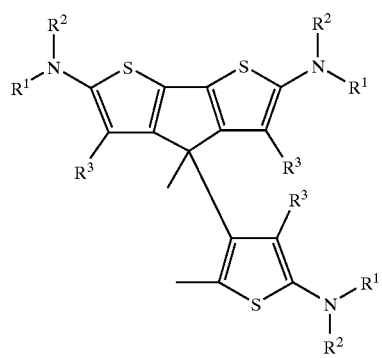

R$^4$ and R$^1$ together form the following group:

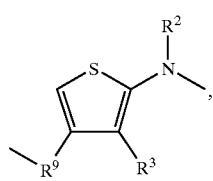

R⁴ and R³ together form the following group:
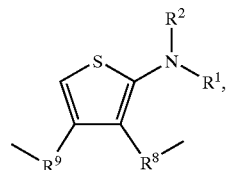
R⁵ and R¹ together form the following group:
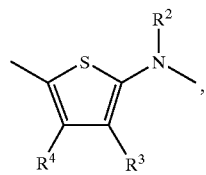
R⁵ and R³ together form the following group:
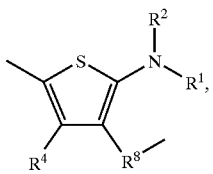
R⁵, R⁴ and R¹ together form one of the following groups:
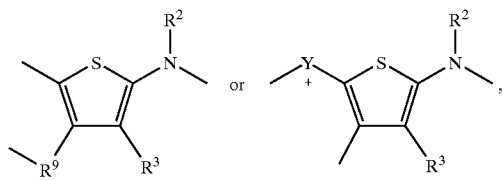
R⁵, R⁴ and R³ together form the following group:
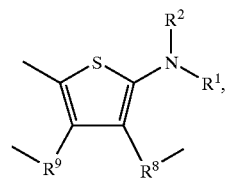
Y in each case denoting CH or N.
2. The thiophene derivative as claimed in claim 1, of the following structure:
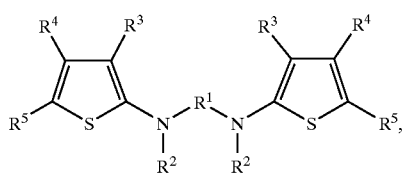
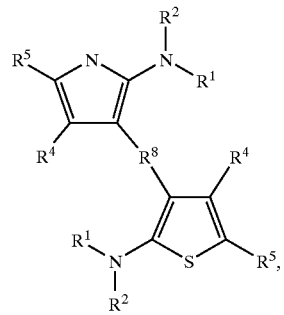
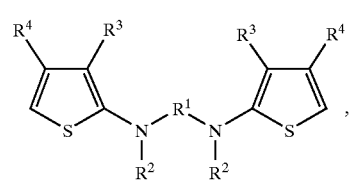
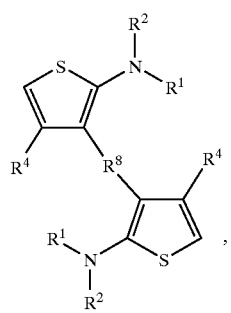
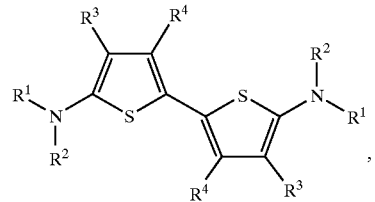
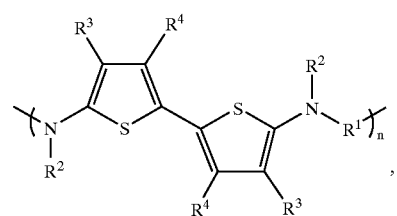
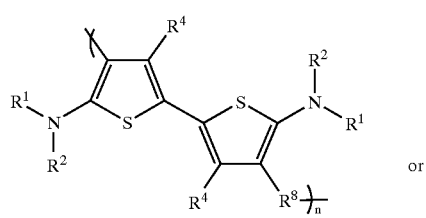
or -continued

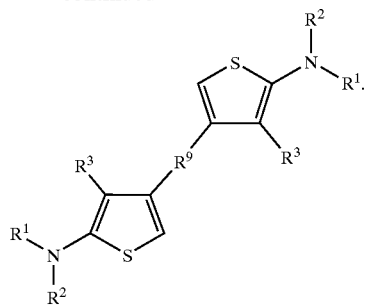

3. The thiophene derivative as claimed in claim 1, of the following structure:

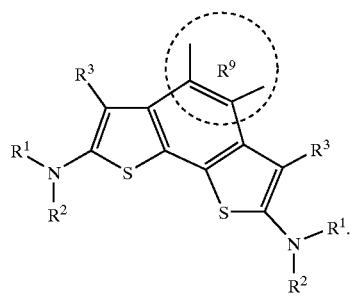

4. The thiophene derivative as claimed in claim 1, of the following structure:

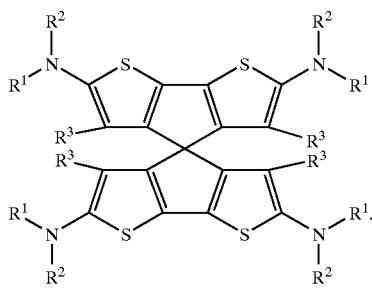

5. The thiophene derivative as claimed in claim 1, of the following structure:

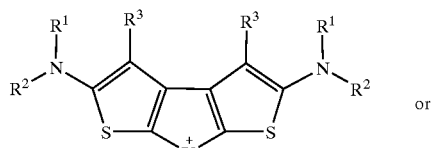

or

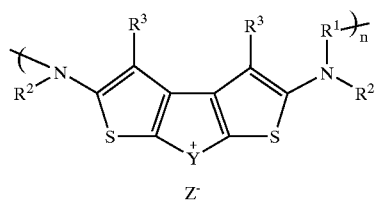

Z denoting an anion and n denoting an integer from 2 to 100.

6. A process for the preparation of a thiophene derivatives as claimed in claim 1, characterized by the following steps:

(a) reaction of a secondary amine with an acyl halide to give a carboxamide;

(b) conversion of the carboxamide into a thiocarboxamide;

(c) reaction of the thiocarboxamide with an α-haloacyl compound to give a 2-(N,N-di(het)arylamino) thiophene deriviative.

7. The process as claimed in claim 6, characterized in that the thiophene derivative is converted oxidatively into a dimer or polymer.

8. The process as claimed in claim 6, characterized in that the thiophene derivative is converted by means of an orthoformic ester or nitrous acid into a polythiophene derivative.

9. An organic light-emitting diode comprising a thiophene derivative of claim 1.

10. An organic photovoltaic component or cell comprising a thiophene derivative of claim 1.

* * * * *